United States Patent

Wolleb

[11] Patent Number: 5,594,128
[45] Date of Patent: Jan. 14, 1997

[54] PROCESS FOR THE PREPARATION OF BROMINATED, ALKOXY-SUBSTITUTED METAL PHTHALOCYANINES

[75] Inventor: Heinz Wolleb, Marly, Switzerland

[73] Assignee: Ciba-Geigy Corporation, Tarrytown, N.Y.

[21] Appl. No.: 530,973

[22] Filed: Sep. 20, 1995

[30] Foreign Application Priority Data

Sep. 23, 1994 [CH]  Switzerland ............................. 2907/94
Nov. 30, 1994 [CH]  Switzerland ............................. 3611/94

[51] Int. Cl.$^6$ ................................................. C09B 47/04
[52] U.S. Cl. .......................................... 540/122; 540/136
[58] Field of Search ................................. 540/122, 136

[56] References Cited

U.S. PATENT DOCUMENTS 5,270,463  12/1993  Itoh et al. .............................. 540/136
5,358,833  10/1994  Itoh et al. .............................. 540/141

FOREIGN PATENT DOCUMENTS 0492508   7/1992   European Pat. Off. .
0513370  11/1992   European Pat. Off. .
0519419  12/1992   European Pat. Off. .
2068993   8/1981   United Kingdom .

OTHER PUBLICATIONS

M. Emmelius et al., pp. 1475–1502, Angewandte Chemie, 1989/11.

Tse Wai Hall et al., pp. 653–658, vol. 6, Nouveau Journal de Chimie, (1982).

F. H. Moser and A. L. Thomas pp. 54–59, Phthalocyanine Compounds (Reinhold Publishing Corporation, New York 1963).

Derwent Abstract 92–069967 of JP 4,015,264.

*Primary Examiner*—Mukund J. Shah
*Assistant Examiner*—Pavanaram K. Sripada
*Attorney, Agent, or Firm*—Michele A. Kovaleski

[57] ABSTRACT

A process for the preparation of a mixture of positionally isomeric brominated tetraalkoxymetal phthalocyanines of the formula I,

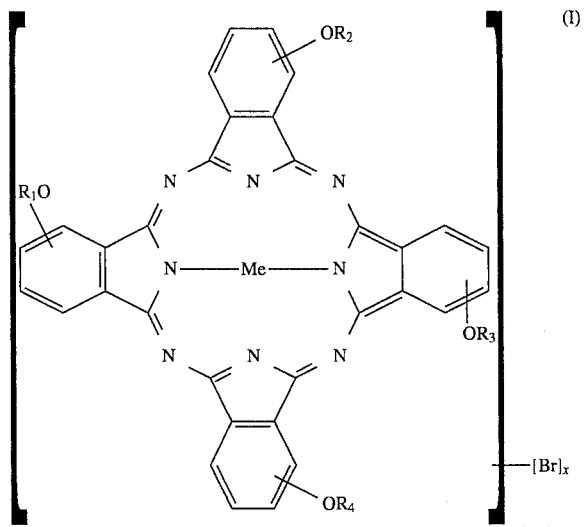

where Me is Cu(II), Pd(II), Zn(II), Sn(II), Ni(II), Co(II), Pb(II), Mn(O) or V(O), x is a number from 1 to 5, and $R_1$ to $R_4$, independently of one another, are linear or branched $C_1$–$C_{16}$alkyl, $C_3$–$C_{16}$alkenyl or $C_3$–$C_{16}$alkynyl radicals which are unsubstituted or substituted by $C_1$–$C_{12}$alkoxy, CN, $NO_2$, halogen, OH, phenyl, cyanophenyl, nitrophenyl, halophenyl, hydroxyphenyl or ($C_1$–$C_{12}$alkoxy)phenyl, by reacting a tetraalkoxy metal phthalocyanine of the formula II with bromine,

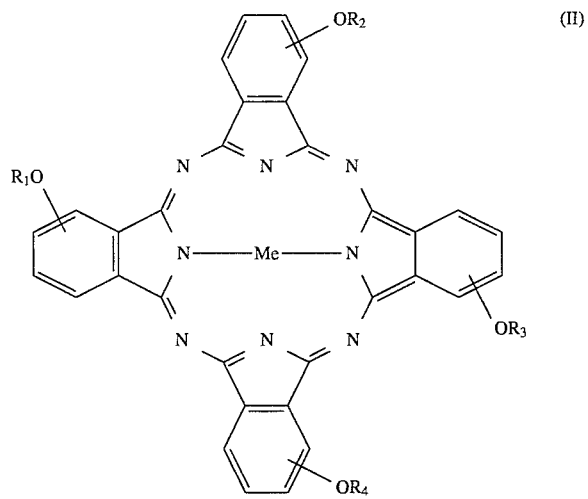

which comprises carrying out the reaction in a halogenated, aromatic solvent, essentially water-immiscible in the presence of a second, aqueous phase.

Substituted phthalocyanines are an important class of dyes for optical information recording, since they have high NIR absorption in the range from 700 nm to 900 nm in the case of appropriate peripheral substitution, depending on the central metal atom.

25 Claims, No Drawings

PROCESS FOR THE PREPARATION OF BROMINATED, ALKOXY-SUBSTITUTED METAL PHTHALOCYANINES

The invention relates to a process for the preparation of brominated, alkoxy-substituted metal phthalocyanines, particularly copper and palladium phthalocyanines.

Substituted phthalocyanines are an important class of dyes for optical information recording, since they have a high NIR absorption in the range from 700 nm to 900 nm when they have appropriate peripheral substitution, depending on the central metal atom.

The use of phthalocyanine dyes which absorb radiation in the near infra-red (NIR) region for recording information in WORM (write once read many) systems has been known for some time and is described, for example, by M. Emmelius in Angewandte Chemie, Issue 11, pages 1475–1502 (1989). The change in absorption necessary for recording information in the form of bits can be achieved by physical modification (for example by sublimation or diffusion) or by chemical modification (for example photochromicity, isomerization or thermal decomposition) by laser irradiation in such recording materials.

Metal complexes, in particular palladium and copper complexes, of alkoxy-substituted, brominated phthalocyanines are likewise known and are described in EP-A-0 513 370 and EP-A-0 519 419. These are halogenated, tetraalkoxy-substituted phthalocyanines which are soluble in organic solvents and whose alkoxy groups contain bulky radicals. The absorption maxima of the compounds described therein are from approx. 700 nm to approx. 730 nm and have a molar absorbance coefficient $\epsilon$ of >100,000 $l \cdot mol^{-1} \cdot cm^{-1}$. These properties allow a sufficiently high refractive index at 780 nm and good sensitivity to be achieved in optical disks produced therewith.

The process for the preparation of these compounds which is described in EP-A-0 513 370 and EP-A-0 519 419 starts from alkoxy-substituted phthalocyanines, which are brominated in an organic solvent which is immiscible with water and is preferably selected from the group consisting of saturated hydrocarbons, ethers and halogenated hydrocarbons.

The $\alpha$- or $\beta$-alkoxy-substituted phthalocyanines required as starting materials in this process can themselves be prepared by methods which are likewise known, as described for example, in Nouveau Journal de Chimie, Vol. 6, pages 653–658 (1982) and in EP-A-0 492 508. These known processes generally each give various positional isomers which have varying solubility in organic solvents. In principle, all mixtures of isomeric $\alpha$- or $\beta$-alkoxy-substituted phthalocyanines are suitable for bromination by the present process. However, preference is given to isomer mixtures which predominantly comprise the readily soluble positional isomers and which can be prepared in high yield if alkoxy-substituted phthalodinitriles are reacted in the presence of nitrobenzene, nitrotoluene or nitroxylene and in the presence of an at least equimolar amount of urea, based on the amount of phthalodinitrile employed.

Brominated tetraalkoxymetal phthalocyanines, in particular the copper and palladium compounds, are themselves important and economical dyes for optical information recording. In addition, they can serve as important intermediates into which, for example, additional phosphorus-containing substituents can subsequently be introduced, allowing the polarity of the compounds and thus their solubility to be matched to a wide variety of solvents.

A high yield in the bromination step is of great importance for economical preparation of these compounds.

Since multiple brominations occur in various positions of the peripheral aromatic carbon skeleton during the reaction, the reproducibility and selectivity of the reaction are likewise of considerable importance. The reaction product must be obtainable highly reproducibly with respect to bromination degree and positions, molar absorbance coefficient and absorption spectrum ($\lambda_{max}$). Any byproducts formed should be produced in very small amounts and be easily removable, so that complex purification methods, for example chromatographic methods, are unnecessary. The undesired byproducts can be, for example, the oxidation products mentioned by F. H. Moser und A. L. Thomas, Phthalocyanine Compounds, pages 54–59 (Reinhold Publishing Corporation, New York 1963).

Although tetraalkoxypalladium phthalocyanines can be brominated in good yield in known solvents such as 1,1,2-trichloroethane, virtually complete, unexpected destruction of the phthalocyanine skeleton is observed in the case of tetraalkoxycopper phthalocyanines, in particular in 1,1,2-trichloroethane.

Surprisingly, it has now been found that brominated tetraalkoxycopper phthalocyanines are obtained in high yield and with a highly reproducible degree of substitution if the corresponding tetraalkoxycopper phthalocyanines are brominated in a halogenated, essentially water-immiscible aromatic solvent in the presence of a second, aqueous phase. The yields are considerably above those achieved when the process is carried out in the solvents described in EP-A-0 513 370 or EP-A-0 519 419.

The aqueous phase is expediently present throughout the bromination reaction; however, it can also be added and removed again periodically. Good mixing of the two phases is preferably ensured, for example by efficient stirring of the reaction mixture or by spraying of one phase into the other.

Surprisingly, even better yields and selectivities are obtained if a reducing agent is added to the aqueous phase. The reducing agent here is preferably not added in one portion at the beginning of the bromination, but instead metered in at such a rate that its concentration just has a reducing action, or particularly preferably is added in portions with interruption of the bromination. This can also be carried out, for example, by first utilizing pure water as the aqueous phase, then temporarily interrupting the supply of bromine and replacing the water phase by a reducing, aqueous solution, and, after further replacement of all or some of the consumed reducing aqueous solution by water, continuing with the supply of bromine. This cycle can be repeated a number of times.

Brominated tetraalkoxypalladium phthalocyanines are likewise obtained in high yield and with highly reproducible degree of substitution by the same process from tetraalkoxypalladium phthalocyanines.

The same process can also be used for the bromination of Cu(II), Pd(II), Zn(II), Sn(II), Ni(II), Co(II), Pb(II), Mn(O) or V(O) tetraalkoxy phthalocyanines.

The invention therefore relates to a process for the preparation of a mixture of positionally isomeric brominated tetraalkoxymetal phthalocyanines of the formula I

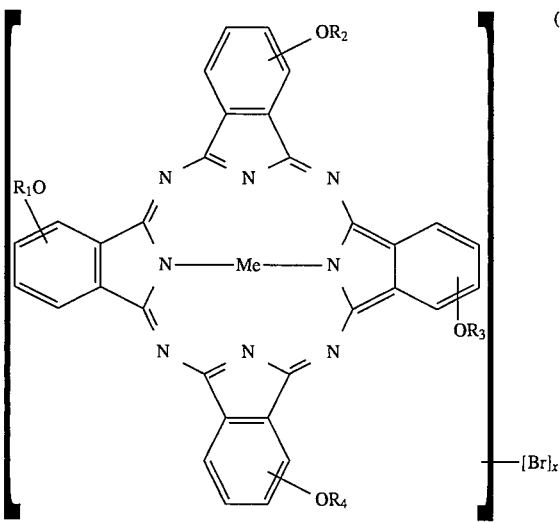

where Me is Cu(II), Pd(II), Zn(II), Sn(II), Ni(II), Co(II), Pb(II), Mn(O) or V(O), x is a number from 1 to 5, and $R_1$ to $R_4$, independently of one another, are linear or branched $C_1$–$C_{16}$alkyl, $C_3$–$C_{16}$alkenyl or $C_3$–$C_{16}$alkynyl radicals which are unsubstituted or substituted by $C_1$–$C_{12}$alkoxy, CN, $NO_2$, halogen, OH, phenyl, cyanophenyl, nitrophenyl, halophenyl, hydroxyphenyl or ($C_1$–$C_{12}$alkoxy)phenyl, by reacting a tetraalkoxy metal phthalocyanine of formula II

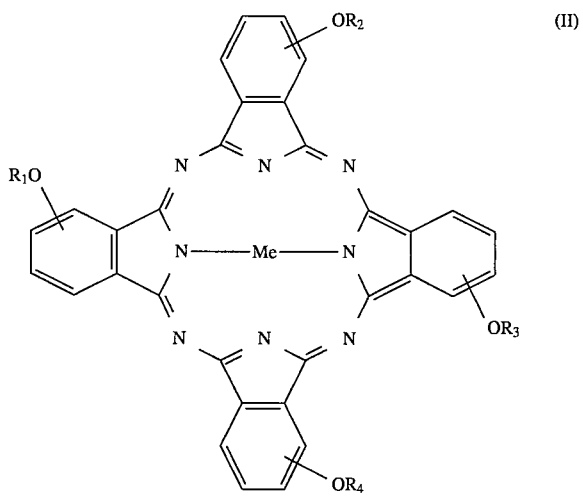

with bromine, which comprises carrying out the reaction in a halogenated, essentially water-immiscible aromatic solvent in the presence of a second, aqueous phase.

In formulae I and II, Me is preferably copper or palladium, most preferably copper. The phthalocyanines of formula I can be substituted by bromine on all 4 phenyl rings of the peripheral aromatic carbon skeleton. At least 2 phenyl rings of the peripheral aromatic carbon skeleton are preferably substituted by bromine. The peripheral aromatic carbon skeleton is preferably substituted by 1 to 4 bromines.

Examples of linear or branched $C_1$–$C_{16}$alkyl radicals are methyl, ethyl and the various positional isomers of propyl, butyl, pentyl, hexyl, heptyl, octyl, nonyl, decyl, undecyl, dodecyl, tridecyl, tetradecyl, pentadecyl and hexadecyl.

Preference is given to $C_4$–$C_{12}$alkyl radicals.

Examples of $C_3$–$C_{16}$alkenyl radicals are propenyl, butenyl, pentenyl, hexenyl, heptenyl, octenyl, nonenyl, decenyl, undecenyl, dodecenyl, tridecenyl, tetradecenyl, pentadecenyl and hexadecenyl with their various positional isomers.

Preference is given to $C_4$–$C_{12}$alkenyl radicals.

Examples of $C_3$–$C_{16}$alkynyl radicals are propynyl, butynyl, pentynyl, hexynyl, heptynyl, octynyl, nonynyl, decynyl, undecynyl, dodecynyl, tridecynyl, tetradecynyl, pentadecynyl and hexadecynyl with their various positional isomers.

Preference is given to $C_4$–$C_{12}$alkynyl radicals.

The alkyl, alkenyl and alkynyl radicals are preferably branched.

Halogen is, for example, fluorine, bromine, chlorine or iodine.

$C_1$–$C_{12}$alkoxy is, for example, methoxy, ethoxy and the various positional isomers of propoxy, butoxy, pentoxy, hexyloxy, heptyloxy, octyloxy, nonyloxy, decyloxy, undecyloxy or dodecyloxy.

Preference is given to $C_1$–$C_8$alkoxy.

$R_1$ to $R_4$ are preferably linear or branched $C_1$–$C_{16}$alkyl radicals which are unsubstituted or substituted by $C_1$–$C_{12}$alkoxy, CN, $NO_2$, halogen, OH, phenyl, cyanophenyl, nitrophenyl, halophenyl, hydroxyphenyl or ($C_1$–$C_{12}$alkoxy)phenyl.

In a particularly preferred sub-group $R_1$ to $R_4$ are linear or branched $C_4$–$C_{12}$alkyl radicals which are unsubstituted or substituted by $C_1$–$C_{12}$alkoxy, CN, $NO_2$, halogen, OH, phenyl, cyanophenyl, nitrophenyl, halophenyl, hydroxyphenyl or($C_1$–$C_{12}$alkoxy)phenyl.

$R_1$ to $R_4$ are very particularly preferably unsubstituted, linear or branched $C_4$–$C_{12}$alkyl radicals, in particular 2,4-dimethyl-3-pentyl.

The substituents —$OR_1$ to —$OR_4$ can be either in the β-position or in the α-position; all substituents —$OR_1$ to —$OR_4$ are preferably in the α-position.

In the case of α- or β-substitution for identical $R_1$ to $R_4$, there are essentially in each case 4 positional isomers which differ in their solubility. If $R_1$ to $R_4$ are different, the number of possible compounds in the product mixture increases.

The present process is particularly highly suitable for the preparation of brominated compounds of the formula I, in which $R_1$ to $R_4$ are identical, principally for the preparation of brominated compounds of formula I, in which $R_1$ to R4 are identical and the substituents —$OR_1$ to —$OR_4$ are each in the α-position.

Preferred halogen-containing aromatic solvents are 1-bromonaphthalene, 1-chloronaphthalene, 1-chloronaphthalene/2-chloronaphthalene, one of the positional isomers of bromotoluene, chlorotoluene or dichlorotoluene, one of the positional isomers of dibromobenzene or dichlorobenzene, bromobenzene or chlorobenzene.

The particularly preferred halogen-containing aromatic solvent is chlorobenzene.

The process is preferably carried out by dissolving bromine in the same halogen-containing aromatic solvent as the compounds of formula II and metering it into the reaction as a solution.

The bromine:halogen-containing aromatic solvent weight ratio is preferably from 1:10 to 10:1, particularly preferably from 1:5 to 5:1.

The process is preferably carried out under a protective-gas atmosphere, for example under nitrogen or argon.

The halogen-containing aromatic solvent:water weight ratio is preferably from 10:1 to 1:10, particularly preferably from 4:1 to 1:1.

The reaction temperature is preferably from 20° C. to 150° C., particularly preferably from 30° C. to 90° C.

The process is preferably carried out under atmospheric pressure.

Any reducing agent in the aqueous phase can be, for example, a water-soluble organic or inorganic reducing agent. Examples of water-soluble organic reducing agents are formaldehyde, hydroquinone and formic and oxalic acids, and salts thereof; examples of water-soluble inorganic reducing agents are phosphorus(III), iron(II), sulfur(IV) and nitrogen compounds, such as triethyl phosphite, iron sulfate heptahydrate, sodium sulfite, potassium sulfite, sodium pyrosulfite, potassium pyrosulfite, sodium thiosulfate, sodium dithionite, sodium dithionate, potassium dithionate, sodium iodide, potassium iodide, hydroxylamine and hydrazine.

Preferred reducing agents are alkali metal sulfites, pyrosulfites and thiosulfates, particularly preferably aqueous sodium sulfite and potassium sulfite solutions.

The examples below illustrate the invention.

Preparation of the Intermediate Compounds

Example A1: Tetra($\alpha$2,4-dimethyl-3-pentoxy)copper phthalocyanine (isomer mixture)

100.0 g (0.41 mol) of 3-(2,4-dimethyl-3-pentoxy)phthalodinitrile, 14,0 g (0,1 mol) copper(II) chloride, 49.6 g (0.82 mol) of urea and 2.0 g (2% by weight) of ammonium molybdate are introduced into 410 ml of nitrobenzene, and the mixture is warmed to 160° C. with stirring under an argon atmosphere and subsequently stirred at this temperature for 5 hours. The mixture is subsequently cooled to RT, diluted with toluene and filtered through a filter aid. The filtrate is evaporated to dryness at 10° C./$10^{-1}$ mbar. The residue is dissolved in 1 l of toluene and filtered through 600 g of silica gel with toluene as eluent. The filtrate is evaporated, and the residue is stirred in 1.5 l of methanol, filtered, washed with methanol and dried overnight at 60° C./165 mbar, giving 99.5 g (94% of theory) of a green-blue solid having a $\lambda_{max}$ of 712 nm ($\epsilon$=197,680 l·mol$^{-1}$·cm$^{-1}$) in N-methylpyrrolidone (NMP). Thin-layer chromatography shows that the isomers I, II and III are present in a ratio of 5:33:62.

Example A2: Tetra($\alpha$-2,4-dimethyl-3-pentoxy)copper phthalocyanine (isomer mixture)

50 g (0.206 mol) of 3-(2,4-dimethyl-3-pentoxy)phthalodinitrile, 7.0 g (51.7 mmol) of copper(II) chloride, 24.8 g (0.413 mol) of urea, 1.0 g (2% by weight) of ammonium molybdate and 200 ml of nitrobenzene are introduced into a 1 l three-neck flask fitted with reflux condenser, magnetic stirrer, thermometer and nitrogen inlet/outlet, and the mixture is stirred at 160° C. for 5 hours with stirring under an inert-gas atmosphere. The reaction mixture is subsequently cooled to RT, diluted with 200 ml of toluene and filtered through a filter aid, and the solid is washed 5× with 100 ml of toluene in each case. The filtrate is filtered through 500 g of silica gel with toluene, and the green fractions are evaporated as far as possible to dryness at 110° C. in a water-pump vacuum, giving 72.1 g of a green resin which still contains a little nitrobenzene and has a $\lambda_{max}$ of 712 nm in NMP.

Example A3: Tetra($\alpha$-2,4-dimethyl-3-pentoxy)palladium phthalocyanine (isomer mixture)

50 g (206 mmol) of 3-(2,4-dimethyl-3-pentoxy)phthalodinitrile, 9.1 g (51.7 mmol) of anhydrous palladium chloride, 24.8 g (413 mmol) of urea and 1 g (2% by weight) of ammonium molybdate are introduced into 200 ml of nitrobenzene, and the mixture is warmed to 160° C. with stirring under an argon atmosphere. The mixture is subsequently stirred at this temperature for 4 hours, then cooled to RT, diluted with toluene and filtered through a filter aid. The filtrate is evaporated to dryness at 100° C./$10^{-1}$ mbar. The residue is taken up in 400 ml of toluene, and the solution is filtered through 500 g of silica gel with toluene as eluent. The toluene phase is evaporated to 250 ml and subsequently added dropwise to 1.5 l of methanol. The precipitate is filtered off, washed twice with 100 ml of methanol and then dried for 12 hours at 60° C./165 mbar, giving 32.5 g (59%) of a green-blue solid having a $\lambda_{max}$ of 702 nm ($\epsilon$=215,190 l·mol$^{-1}$·cm$^{-1}$) in NMP. NMR shows that the isomers I, II and III are present in a ratio of 5:53:42.

Preparation of the End Products

Example B1: brominated tetra($\alpha$-2,4-dimethyl-3-pentoxy)copper phthalocyanine 2 g (1.94 mmol) tetra($\alpha$-2,4-dimethyl-3-pentoxy)copper phthalocyanine, prepared as described in Example A1, are introduced into 20 g of chlorobenzene and 10 g of water. 0.96 g (6,0 mmol) of bromine in 1 g of chlorobenzene are added dropwise over the course of ten minutes at 40° C. with stirring under an argon atmosphere, and the mixture is subsequently stirred at 60° C. for 1 hour. The reaction mixture is cooled, diluted with 50 ml of chlorobenzene, washed once with 50 ml of aqueous 3% NaHSO$_3$, dried over MgSO$_4$, filtered and evaporated. The residue is dissolved in toluene and filtered through 50 g of silica gel with toluene. The filtrate is evaporated to dryness and dried overnight at 60° C./165 mbar, giving 2.0 g (84.7% of theory) of a green powder having a $\lambda_{max}$ of 727 nm in NMP ($\epsilon$=145,584 l·mol$^{-1}$·cm$^{-1}$) and a bromine content of 17.2%.

Example B2: brominated tetra($\alpha$-2,4-dimethyl-3-pentoxy)copper phthalocyanine The crude product from Example A2 is introduced into 735 g of chlorobenzene and 362 g of water in a 2.5 l multineck flask fitted with an anchor stirrer, thermometer, reflux condenser and dropping funnel, and the mixture is warmed to 40° C. with stirring. 7.81 g (48.9 mmol) of bromine in 20 g of chlorobenzene are then added dropwise over the course of 30 minutes, and the mixture is stirred at the same temperature for 1 hour. The solution has a $\lambda_{max}$ of 715 nm in NMP. 300 ml of 3% NaHSO$_3$ solution are added, and the mixture is stirred for 5 minutes. The aqueous phase is aspirated off, then 300 ml of water are added, the mixture is stirred briefly, and the aqueous phase is aspirated off again. A further 362 g of water are then added, and, as described above, 7.81 g (48.9 mmol) of bromine are added dropwise. These operations are repeated until a total 25.77 g (0.161 mol) of bromine have been reacted and the solution has a $\lambda_{max}$ of 722 nm in NMP. The solution is cooled, the phases are separated, and the organic phase is dried over magnesium sulfate. The solution is filtered through 300 g of silica gel with toluene, and the green fraction is evaporated at 110° C. in a water-pump vacuum. The residue is taken up in 100 ml of toluene, and the solution is added dropwise to 2 l of methanol with stirring. The precipitate is filtered off, washed 3 times with 100 ml of methanol in each case and dried overnight at 60° C./165 mbar, giving 44.22 g (70.6% of theory over 2 steps) of a green solid having a $\lambda_{max}$ of 722 nm in NMP ($\epsilon$=172,510 l·mol$^{-1}$·cm$^{-1}$) and a bromine content of 15.18%.

Example B3: brominated tetra($\alpha$-2,4-dimethyl-3-pentoxy)palladium phthalocyanine 10 g (9.30 mmol) of tetra($\alpha$-2,4-dimethyl-3-pentoxy)palladium phthalocyanine, prepared as described in Example A3, are introduced into 100 g of chlorobenzene and 50 g of water in a 500 ml multineck flask fitted with anchor stirrer, thermometer, reflux condenser and dropping funnel, and the mixture is warmed to 40° C. with stirring. 7.4 g (46.48 mmol) of bromine in 2 g of chlorobenzene are then added dropwise over the course of 10 minutes, and the mixture is stirred at 60° C. for 1 hour. The solution is cooled, diluted with 100 ml of chlorobenzene and washed with 50 ml of 3% NaHSO$_3$ solution. The organic phase is dried over magnesium sulfate and evaporated. The green residue is dissolved in toluene, the solution is filtered through 200 g of silica gel with toluene, the green fraction is evaporated to 80 ml in a water-pump vacuum. This solution is added dropwise to 700 ml of methanol with stirring. The precipitate is filtered off, washed 3× with 50 ml of methanol in each case and dried overnight at 60° C./165 mbar, giving 11.6 g (88.1% of theory) of a green solid having a $\lambda_{max}$ of 724 nm in NMP ($\epsilon$=163,210 l·mol$^{-1}$·cm$^{-1}$) and a bromine content of 24.24%.

Comparative Example

Comparative Example V1 (to Example B1)

Bromination of tetra(α-2,4-dimethyl-3-pentoxy)copper phthalocyanine 2 g (1.94 mmol) of tetra(α-2,4-dimethyl-3-pentoxy)copper phthalocyanine, prepared as described in Example A1, are introduced into 20 g 1,1,2-trichloroethane and 11 g of water. 0.82 g (5.11 mmol) of bromine in 2 g of 1,1,2-trichloroethane are added dropwise over the course of 25 minutes at 40° C. with stirring under an argon atmosphere. The reaction mixture decomposes to give a brown solution. Thin-layer chromatography and UV/VIS spectroscopy show neither starting material nor target product as for Examples B1 or B2.

What is claimed is:

1. A process for the preparation of a mixture of positionally isomeric brominated tetraalkoxymetal phthalocyanines of the formula I

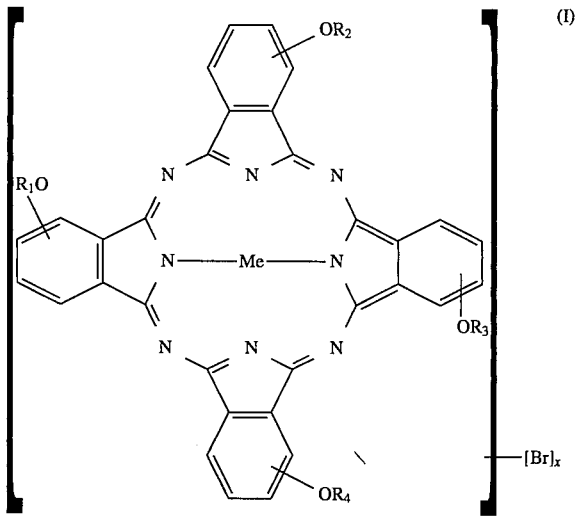

where Me is Cu(II), Pd(II), Zn(II), Sn(II), Ni(II), Co(II), Pb(II), Mn(O) or V(O), x is a number from 1 to 5, and R$_1$ to R$_4$, independently of one another, are linear or branched C$_1$–C$_{16}$alkyl, C$_3$–C$_{16}$alkenyl or C$_3$–C$_{16}$alkynyl radicals which are unsubstituted or substituted by C$_1$–C$_{12}$alkoxy, —CN, NO$_2$, halogen, —OH, phenyl, cyanophenyl, nitrophenyl, halophenyl, hydroxyphenyl or (C$_1$–C$_{12}$alkoxy)phenyl, by reacting a tetraalkoxy metal phthalocyanine of the formula II

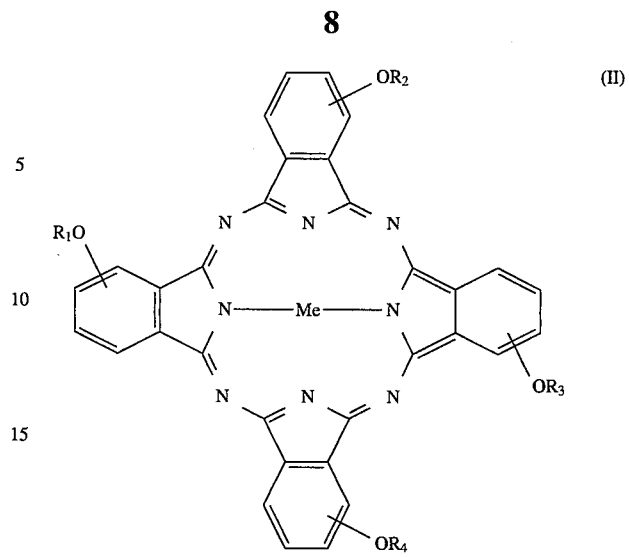

with bromine, which comprises carrying out the reaction in a halogenated, essentially water-immiscible aromatic solvent in the presence of a second, aqueous phase.

2. A process according to claim 1, in which R$_1$ to R$_4$ are linear or branched C$_1$–C$_{16}$alkyl radicals, which are unsubstituted or substituted by C$_1$–C$_{12}$alkoxy, CN, NO$_2$, halogen, OH, phenyl, cyanophenyl, nitrophenyl, halophenyl, hydroxyphenyl or (C$_1$–C$_{12}$alkoxy)phenyl.

3. A process according to claim 2, in which R$_1$ to R$_4$ are linear or branched C$_4$–C$_{12}$alkyl radicals, which are unsubstituted or substituted by C$_1$–C$_{12}$alkoxy, CN, NO$_2$, halogen, OH, phenyl, cyanophenyl, nitrophenyl, halophenyl, hydroxyphenyl or (C$_1$–C$_{12}$alkoxy)phenyl.

4. A process according to claim 3, in which R$_1$ to R$_4$ are unsubstituted linear or branched C$_4$–C$_{12}$ alkyl radicals.

5. A process according to claim 4, in which R$_1$ to R$_4$ are identical.

6. A process according to claim 5 in which R$_1$ to R$_4$ are 2,4-dimethyl-3-pentyl.

7. A process according to claim 1, in which the substituents —OR$_1$ to —OR$_4$ are in the α-position.

8. A process according to claim 1, in which at least 2 phenyl rings of the peripheral aromatic carbon skeleton are substituted by bromine.

9. A process according to claim 1, in which Me is copper or palladium.

10. A process according to claim 1, in which Me is copper.

11. A process according to claim 1, in which the halogen-containing aromatic solvent is 1-bromonaphthalene, 1-chloronaphthalene, 1-chloronaphthalene/2-chloronaphthalene, one of the positional isomers of bromotoluene, chlorotoluene or dichlorotoluene, one of the positional isomers of dibromobenzene or dichlorobenzene, bromobenzene or chlorobenzene.

12. A process according to claim 11, in which the halogen-containing aromatic solvent is chlorobenzene.

13. A process according to claim 1, in which bromine is dissolved in the same halogen-containing aromatic solvent as the compounds of the formula II, and is metered into the reaction as a solution.

14. A process according to claim 13, in which the bromine:halogen-containing aromatic solvent weight ratio is from 1:10 to 10:1.

15. A process according to claim 14, in which the bromine:halogen-containing aromatic solvent weight ratio is from 1:5 to 5:1.

16. A process according to claim 1, in which the reaction is carried out under an inert gas atmosphere.

17. A process according to claim 1, in which the halogen-containing aromatic solvent:water weight ratio is from 10:1 to 1:10.

18. A process according to claim 17 in which the halogen-containing aromatic solvent:water weight ratio is from 4:1 to 1:1.

19. A process according to claim 1, in which the reaction is carried out at a temperature of from 20° C. to 150° C.

20. A process according to claim 19, in which the reaction is carried out from 30° C. to 90° C.

21. A process according to claim 1, which is carried out at atmospheric pressure.

22. A process according to claim 1, in which the two phases are mixed well.

23. A process according to claim 1, in which the aqueous phase contains a reducing agent.

24. A process according to claim 23, in which the reducing agent is an alkali metal sulfite, pyrosulfite or thiosulfite.

25. A process according to claim 23, in which the reducing agent is added in portions with interruption of the bromination.

* * * * *